(12) United States Patent
Sartor

(10) Patent No.: US 7,537,594 B2
(45) Date of Patent: May 26, 2009

(54) SUCTION COAGULATOR WITH DISSECTING PROBE

(75) Inventor: Joe Don Sartor, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 800 days.

(21) Appl. No.: 10/832,882

(22) Filed: Apr. 27, 2004

(65) Prior Publication Data

US 2004/0260280 A1  Dec. 23, 2004

Related U.S. Application Data

(60) Provisional application No. 60/467,182, filed on May 1, 2003.

(51) Int. Cl.
*A61B 18/18* (2006.01)

(52) U.S. Cl. .......................... 606/49; 606/41

(58) Field of Classification Search ............. 606/41, 606/45–50
See application file for complete search history.

(56) References Cited

U.S. PATENT DOCUMENTS

| | | | |
|---|---|---|---|
| 3,980,086 A | 9/1976 | Kletschka et al. | |
| 4,493,694 A | 1/1985 | Wuchinich | |
| 4,512,344 A | 4/1985 | Barber | |
| RE32,066 E * | 1/1986 | Leveen | 607/154 |
| 4,567,882 A | 2/1986 | Heller | |
| 4,573,979 A | 3/1986 | Blake | |
| 4,660,571 A | 4/1987 | Hess et al. | |
| 4,662,367 A | 5/1987 | Gore, Jr. | |
| 4,683,884 A | 8/1987 | Hatfield et al. | |
| 4,804,364 A | 2/1989 | Dieras et al. | |
| 4,823,791 A | 4/1989 | D'Amelio et al. | |
| 4,869,715 A | 9/1989 | Sherburne | |
| 4,909,249 A | 3/1990 | Akkas et al. | |
| 4,927,420 A * | 5/1990 | Newkirk et al. | 606/45 |
| 4,932,952 A | 6/1990 | Wojciechowicz, Jr. | |
| RE33,258 E | 7/1990 | Onik et al. | |
| 4,949,734 A * | 8/1990 | Bernstein | 128/897 |
| 4,982,734 A | 1/1991 | Green et al. | |
| 5,007,908 A * | 4/1991 | Rydell | 606/47 |
| 5,009,656 A | 4/1991 | Reimels | |
| 5,035,695 A * | 7/1991 | Weber et al. | 606/42 |
| 5,060,658 A * | 10/1991 | Dejter, et al. | 600/566 |
| 5,084,045 A * | 1/1992 | Helenowski | 606/32 |
| 5,084,052 A | 1/1992 | Jacobs | |
| 5,089,002 A | 2/1992 | Kirwan, Jr. | |
| 5,116,333 A | 5/1992 | Beane | |
| 5,123,902 A | 6/1992 | Muller et al. | |

(Continued)

FOREIGN PATENT DOCUMENTS

JP     56-9856 U     1/1981

(Continued)

*Primary Examiner*—Michael Peffley

(57) ABSTRACT

An electrosurgical suction coagulator includes a handle having an elongated tube electrode or conductive suction tube extending from a distal end of the handle. The elongated suction tube includes a substantially blunt or closed distal end and an elongated slot disposed therethrough for slideably receiving a needle electrode. The needle electrode is selectively extendible relative to the closed distal end to facilitate precise dissection. When retracted, the user can use the closed distal end for spot or blunt coagulation. At least one aspiration port is disposed along a side of the elongated suction tube for removing surgical fluids from the operating area.

13 Claims, 5 Drawing Sheets

U.S. PATENT DOCUMENTS

| | | | |
|---|---|---|---|
| 5,123,904 A | | 6/1992 | Shimomura et al. |
| 5,133,714 A | | 7/1992 | Beane |
| 5,167,622 A | | 12/1992 | Muto |
| 5,180,363 A | | 1/1993 | Idemoto et al. |
| 5,186,714 A | * | 2/1993 | Boudreault et al. ............ 604/21 |
| 5,188,102 A | | 2/1993 | Idemoto et al. |
| 5,190,541 A | | 3/1993 | Abele et al. |
| 5,203,769 A | | 4/1993 | Clement et al. |
| 5,246,440 A | | 9/1993 | Van Noord |
| 5,248,297 A | | 9/1993 | Takase |
| 5,267,994 A | * | 12/1993 | Gentelia et al. ................ 606/15 |
| 5,277,696 A | | 1/1994 | Hagen |
| 5,290,282 A | | 3/1994 | Casscells |
| 5,290,285 A | | 3/1994 | Kirwan, Jr. |
| 5,300,022 A | | 4/1994 | Klapper et al. |
| 5,312,401 A | | 5/1994 | Newton et al. |
| 5,334,140 A | | 8/1994 | Phillips |
| 5,342,357 A | * | 8/1994 | Nardella ....................... 606/40 |
| 5,360,425 A | * | 11/1994 | Cho ............................... 606/8 |
| 5,360,428 A | | 11/1994 | Hutchinson, Jr. |
| 5,364,395 A | | 11/1994 | West, Jr. |
| 5,366,476 A | | 11/1994 | Noda |
| 5,368,560 A | | 11/1994 | Rambo et al. |
| 5,370,675 A | * | 12/1994 | Edwards et al. ............. 607/101 |
| 5,376,089 A | | 12/1994 | Smith |
| 5,380,277 A | | 1/1995 | Phillips |
| 5,380,320 A | | 1/1995 | Morris |
| 5,383,876 A | | 1/1995 | Nardella |
| 5,391,144 A | | 2/1995 | Sakurai et al. |
| 5,395,315 A | | 3/1995 | Griep |
| 5,401,274 A | * | 3/1995 | Kusunoki ..................... 606/41 |
| 5,403,311 A | * | 4/1995 | Abele et al. ................... 606/49 |
| 5,415,657 A | | 5/1995 | Taymor-Luria |
| 5,423,814 A | | 6/1995 | Zhu et al. |
| 5,437,665 A | * | 8/1995 | Munro ......................... 606/47 |
| 5,441,482 A | | 8/1995 | Clague et al. |
| 5,441,499 A | * | 8/1995 | Fritzsch ....................... 606/45 |
| 5,451,222 A | | 9/1995 | DeMaagd et al. |
| 5,462,521 A | | 10/1995 | Brucker et al. |
| 5,464,389 A | | 11/1995 | Stahl |
| 5,472,441 A | | 12/1995 | Edwards et al. |
| 5,480,397 A | | 1/1996 | Eggers et al. |
| 5,480,398 A | | 1/1996 | Eggers |
| 5,484,434 A | | 1/1996 | Cartmell et al. |
| 5,490,836 A | | 2/1996 | Desai |
| 5,496,314 A | | 3/1996 | Eggers |
| 5,514,086 A | | 5/1996 | Parisi et al. |
| 5,520,685 A | | 5/1996 | Wojciechowicz |
| 5,549,604 A | | 8/1996 | Sutcu et al. |
| 5,558,634 A | | 9/1996 | Mitchell |
| 5,562,609 A | | 10/1996 | Brumbach |
| 5,562,659 A | | 10/1996 | Morris |
| 5,599,345 A | * | 2/1997 | Edwards et al. ............... 606/41 |
| 5,605,539 A | | 2/1997 | Buelna et al. |
| 5,620,440 A | | 4/1997 | Heckele et al. |
| 5,634,924 A | | 6/1997 | Turkel et al. |
| 5,645,537 A | | 7/1997 | Powles et al. |
| 5,662,647 A | | 9/1997 | Crow et al. |
| 5,665,101 A | | 9/1997 | Becker et al. |
| 5,667,489 A | | 9/1997 | Kraff et al. |
| 5,669,876 A | | 9/1997 | Schechter et al. |
| 5,672,173 A | | 9/1997 | Gough et al. |
| 5,693,044 A | | 12/1997 | Cosmescu |
| 5,695,495 A | | 12/1997 | Ellman et al. |
| 5,697,926 A | | 12/1997 | Weaver |
| 5,702,387 A | | 12/1997 | Arts et al. |
| 5,709,675 A | | 1/1998 | Williams |
| 5,718,677 A | | 2/1998 | Capetan et al. |
| 5,718,701 A | | 2/1998 | Shai et al. |
| 5,718,702 A | | 2/1998 | Edwards |
| 5,720,745 A | | 2/1998 | Farin et al. |
| 5,725,495 A | | 3/1998 | Strukel et al. |
| 5,730,718 A | | 3/1998 | Anis et al. |
| 5,730,742 A | | 3/1998 | Wojciechowicz |
| 5,730,752 A | | 3/1998 | Alden et al. |
| 5,735,833 A | | 4/1998 | Olson |
| 5,741,226 A | | 4/1998 | Strukel et al. |
| 5,743,871 A | | 4/1998 | Strukel et al. |
| 5,744,360 A | | 4/1998 | Hu et al. |
| 5,755,700 A | | 5/1998 | Kritzinger et al. |
| 5,766,194 A | | 6/1998 | Smith |
| 5,776,092 A | | 7/1998 | Farin et al. |
| 5,782,795 A | | 7/1998 | Bays |
| 5,785,678 A | | 7/1998 | Griep et al. |
| 5,792,167 A | | 8/1998 | Kablik et al. |
| 5,807,307 A | | 9/1998 | Parisi et al. |
| 5,807,310 A | | 9/1998 | Hood |
| 5,807,395 A | * | 9/1998 | Mulier et al. .................. 606/41 |
| 5,810,805 A | | 9/1998 | Sutcu et al. |
| 5,810,806 A | | 9/1998 | Ritchart et al. |
| 5,814,044 A | | 9/1998 | Hooven |
| 5,827,275 A | | 10/1998 | Morris |
| 5,845,646 A | | 12/1998 | Lemelson |
| 5,846,219 A | | 12/1998 | Vancaillie |
| 5,876,400 A | * | 3/1999 | Songer ........................ 606/45 |
| 5,885,281 A | | 3/1999 | Urueta |
| 5,891,141 A | | 4/1999 | Rydell |
| 5,893,849 A | | 4/1999 | Weaver |
| 5,895,386 A | * | 4/1999 | Odell et al. .................... 606/50 |
| 5,904,681 A | | 5/1999 | West, Jr. |
| 5,906,615 A | | 5/1999 | Thompson |
| 5,908,419 A | | 6/1999 | Hahnen et al. |
| 5,911,700 A | | 6/1999 | Mozsary et al. |
| 5,913,857 A | * | 6/1999 | Ritchart et al. ................ 606/45 |
| 5,916,215 A | | 6/1999 | Long et al. |
| 5,919,190 A | | 7/1999 | VanDusseldorp |
| 5,919,191 A | | 7/1999 | Lennox et al. |
| 5,925,039 A | | 7/1999 | Landingham |
| 5,925,040 A | | 7/1999 | Nardella et al. |
| 5,925,041 A | | 7/1999 | Long et al. |
| 5,925,043 A | | 7/1999 | Kumar et al. |
| 5,925,044 A | | 7/1999 | Hofmann et al. |
| 5,925,045 A | | 7/1999 | Reimels et al. |
| 5,931,848 A | | 8/1999 | Saadat |
| 5,944,716 A | | 8/1999 | Hektner |
| 5,944,718 A | | 8/1999 | Austin et al. |
| 5,947,988 A | | 9/1999 | Smith |
| 5,951,546 A | | 9/1999 | Lorentzen |
| 5,951,548 A | | 9/1999 | DeSisto et al. |
| 5,951,551 A | | 9/1999 | Erlich |
| 5,957,882 A | * | 9/1999 | Nita et al. ..................... 604/22 |
| 5,957,921 A | | 9/1999 | Mirhashemi et al. |
| 5,957,928 A | | 9/1999 | Kirwan, Jr. |
| 5,964,754 A | | 10/1999 | Osypka |
| 5,964,758 A | | 10/1999 | Dresden |
| 5,968,008 A | * | 10/1999 | Grams ......................... 604/35 |
| 5,968,042 A | | 10/1999 | Ernster |
| 5,972,013 A | * | 10/1999 | Schmidt ..................... 606/185 |
| 5,984,937 A | | 11/1999 | Morse et al. |
| 5,989,249 A | | 11/1999 | Kirwan, Jr. |
| 6,001,094 A | | 12/1999 | Edwards et al. |
| 6,004,317 A | | 12/1999 | Speiser |
| 6,007,533 A | | 12/1999 | Casscells et al. |
| 6,015,406 A | | 1/2000 | Goble et al. |
| 6,020,196 A | | 2/2000 | Hu et al. |
| 6,027,501 A | | 2/2000 | Goble et al. |
| 6,030,381 A | | 2/2000 | Jones et al. |
| 6,030,383 A | | 2/2000 | Benderev |
| 6,032,673 A | | 3/2000 | Savage et al. |
| 6,033,375 A | | 3/2000 | Brumbach |
| 6,033,376 A | | 3/2000 | Rockley |
| 6,033,400 A | | 3/2000 | Grossi et al. |
| 6,033,402 A | | 3/2000 | Tu et al. |
| 6,039,734 A | | 3/2000 | Goble |

| | | |
|---|---|---|
| 6,039,735 A | 3/2000 | Greep |
| 6,042,581 A | 3/2000 | Ryan et al. |
| 6,053,912 A | 4/2000 | Panescu et al. |
| 6,056,746 A * | 5/2000 | Goble et al. ............... 606/48 |
| 6,056,747 A | 5/2000 | Saadat et al. |
| 6,059,783 A | 5/2000 | Kirwan, Jr. |
| 6,063,079 A | 5/2000 | Hovda et al. |
| 6,063,081 A * | 5/2000 | Mulier et al. ............... 606/45 |
| 6,066,137 A | 5/2000 | Greep |
| 6,080,151 A | 6/2000 | Swartz et al. |
| 6,117,151 A | 9/2000 | Urich et al. |
| 6,132,436 A | 10/2000 | Portney |
| 6,179,803 B1 * | 1/2001 | Edwards et al. ............... 604/22 |
| 6,256,859 B1 | 7/2001 | Stoddard et al. |
| 6,336,925 B1 | 1/2002 | Malak |
| 6,346,107 B1 * | 2/2002 | Cucin ............... 606/49 |
| 6,361,532 B1 | 3/2002 | Burek |
| 6,383,203 B1 | 5/2002 | Makihara |
| 6,398,754 B1 | 6/2002 | Sutton et al. |
| 6,406,476 B1 * | 6/2002 | Kirwan et al. ............... 606/50 |
| 6,428,498 B2 | 8/2002 | Uflacker |
| 6,428,499 B1 | 8/2002 | Halverson |
| 6,458,126 B1 | 10/2002 | Doyle |
| 6,770,070 B1 * | 8/2004 | Balbierz ............... 606/41 |
| 6,958,056 B2 * | 10/2005 | Kadziauskas et al. ....... 604/272 |
| 2001/0012935 A1 * | 8/2001 | Morgan et al. ............... 606/41 |
| 2002/0111564 A1 * | 8/2002 | Burbank et al. ............... 600/567 |
| 2003/0065316 A1 * | 4/2003 | Levine et al. ............... 606/33 |

FOREIGN PATENT DOCUMENTS

| | | |
|---|---|---|
| JP | 57-7864 | 1/1982 |
| JP | 57-21493 Y2 | 5/1982 |
| JP | 2-94452 U | 7/1990 |
| JP | 6-70503 A | 3/1994 |

* cited by examiner

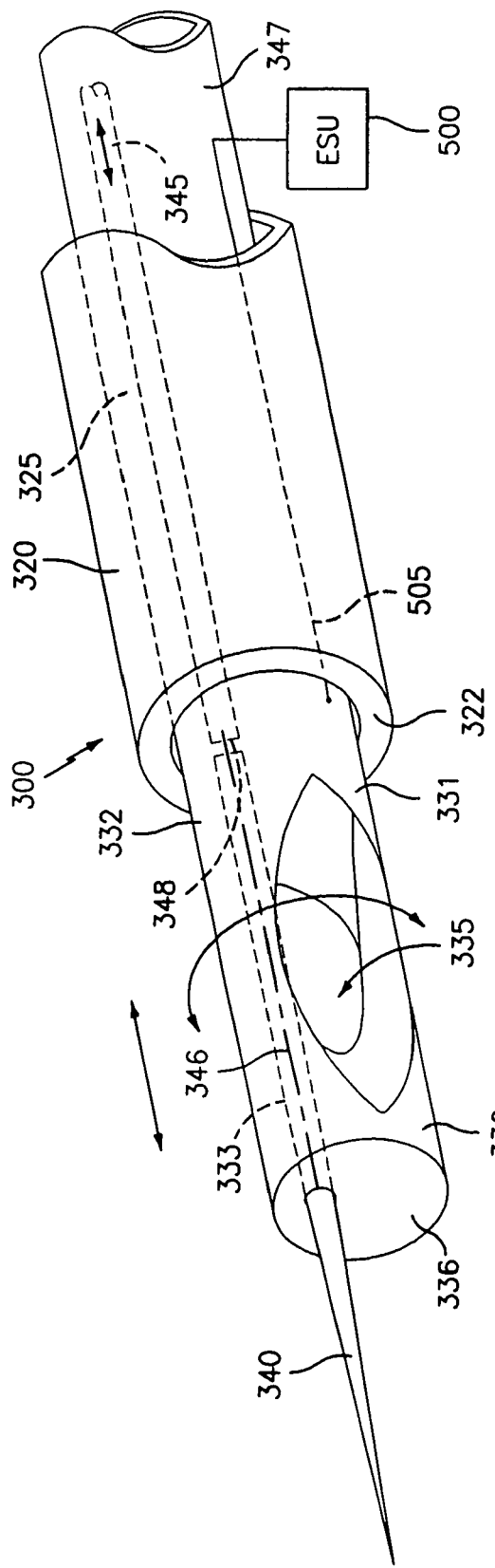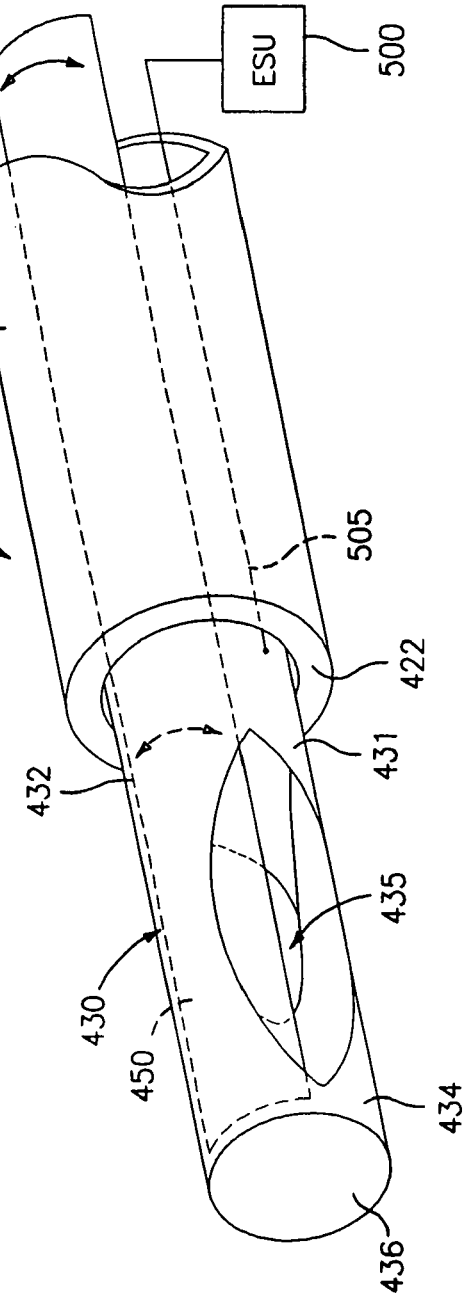

SUCTION COAGULATOR WITH DISSECTING PROBE

CROSS REFERENCE TO RELATED APPLICATION

The present application claims the benefit of priority to U.S. Provisional Application Ser. No. 60/467,182 filed on May 1, 2003 by Joe Sartor, the entire contents of which being incorporated by reference herein.

BACKGROUND

The present invention relates generally to electrosurgical coagulators and, more particularly to an electrosurgical suction coagulator having a selectively extendible dissecting probe attached to a distal end thereof.

TECHNICAL FIELD

The coagulation of bleeding blood vessels and tissue using electrically conductive suction tubes is a technique which has been widely used for some time. Typically, a combination electrocautery and suction device is employed in surgery wherever excessive blood must be removed from the bleeding site in order to facilitate hemostasis of any bleeding vessels. More particularly, during any given surgical procedure, several layers of tissue usually must be penetrated to reach the operative field. When excising an organ, such as a gallbladder, the tissue surrounding the organ must be penetrated and dissected before the organ can be removed. The tissues being dissected, however, often contain blood vessels, nerves, lymph vessels, and the like, which should not be severed. The technique of blunt dissection is often used to prevent unnecessary damage caused by severing these vessels or nerves.

Blunt dissection, as opposed to sharp dissection, involves the use of a blunt surface to break through the tissue, thereby preventing the damage and bleeding caused by lasers and scalpels, the tools of sharp dissection. Hard surgical sponges, generally known as peanuts or Kittner sponges, or a surgeon's fingers are often used as blunt dissectors. A peanut is a tightly wound ball of absorbent material, such as gauze or other woven cotton, which is typically gripped with forceps and acts to abrade the tissue being dissected so that the dissection can be performed by either pulling on the tissue or by forcing the peanut through the tissue.

Laparoscopy, surgery performed through several small incisions made in the body rather than through a single large opening, is quickly becoming the preferred method of performing certain procedures due to the reduced trauma and risk of infection as compared to normal, open surgical procedures. As a result, the use of conventional blunt dissectors, such as the peanut, during laparoscopic procedures presents many significant drawbacks. For instance, peanuts, being secured only by forceps, can become loose in the body. Further, the view of the operative field often becomes obstructed by pieces of tissue, blood and other bodily fluids produced during blunt dissection, necessitating the immediate need for both irrigation and aspiration of the operative field. Since it is undesirable to create additional incisions, the dissection must be stopped, the dissector must be removed, and an irrigator and/or aspirator must be inserted to remove the fluid and debris.

Electrosurgical suction coagulators which both coagulate and dissect tissue have also been available for some time. Generally, these devices include a conductive suction tube having an insulating coating over all but a most distal portion of the tube so that the distal portion forms a generally annular ablating electrode. The distal end can be used as a blunt dissection device and/or a blunt coagulator. A suction source is attached to a proximal portion of the tube for evacuating excess fluid and debris from the surgical site through the distal end of the tube. While known electrosurgical devices are used to effect hemostasis, such devices have not been optimized and, in particular, the electrodes do not provide for precision coagulation of tissue. In other words, the very nature and configuration of the ring-like electrodes do not allow for precise dissection, ablation or coagulation of tissue, i.e., circular, ring electrodes are blunt and do not provide precise electrode control.

Moreover, it is known that ring-like electrosurgical suction coagulators can clog at the distal end with blood or tissue during operation, interrupting the hemostasis procedure and requiring additional effort by the operating physician and staff. The suction prevents the electrode from moving smoothly over a target area. A vacuum port on the handle may be employed to selectively reduce the amount of suction during activation, however, the suction effect at the end is not eliminated. As evident in use, the clog occurs from eschar buildup on the end of the suction tube where the electrosurgical heat is being created. Further, it is believed that the heat cannot be properly dissipated when the opening is occluded by the tissue targeted for the electrosurgical effect.

Ventilation ports also tend to hinder 360 degree operation of a device, in that a physician cannot easily rotate a device while maintaining his/her finger over the ventilation port. By and large, these devices are expensive, cumbersome and difficult to manipulate in the operating field and often require cleaning during the surgical procedure thus requiring the surgeon to remove the instrument from the operating cavity for cleaning.

Thus there exists a need to develop a coagulating and dissecting instrument that can dissect tissue in a more precise manner and which is less prone to clogging during use. Such a device would be a welcome advance in the art, particularly when such benefits are realized in a rugged, reliable, and relatively simple design.

SUMMARY

The surgical coagulator according to the present disclosure includes a handle having an elongated conductive tube-like electrode or suction tube electrode extending from a distal end of the handle. The elongated suction tube includes a substantially blunt or closed distal end for delivering coagulating current to the operating area for blunt or gross dissection. An elongated slot is disposed through the suction tube electrode and is dimensioned to slideably receiving a needle or wire electrode. The needle electrode is selectively extendible relative to the closed distal end to facilitate precise dissection. When the needle electrode is retracted, the user can use the blunt distal end for blunt coagulation and dissection. At least one aspiration port is disposed along a side of the suction tube electrode for removing surgical fluids and debris from the operating area. Preferably, the port or ports are positioned circumferentially around the suction tube electrode to prevent obstructing the tube when coagulating tissue.

Preferably, the needle electrode and/or the suction tube electrode are substantially flexible or malleable to facilitate dissection and manipulation of the coagulator in the operating field. The needle electrode may be manufactured by plant cutting a small gauge wire which may be made from a refractory alloy or the like. In one embodiment, the coagulator includes one aspiration port which extends generally from a proximal end of the suction tube electrode to the distal end of the suction tube electrode. In another embodiment, the suction tube electrode includes one aspiration port which extends transversally through the suction tube electrode.

Preferably, the coagulator includes at least one control switch for activating the suction tube electrode and/or the needle electrode either independently or concurrently. Alternatively, the coagulator may include a series of switches, dials and/or slide switches for controlling one or both of the electrodes in terms of waveform, intensity, voltage, current, surgical effect, etc.

Another embodiment of the present disclosure includes a surgical coagulator having a handle which includes an elongated suction electrode extending from a distal end thereof which is selectively energizable by the user to accomplish a surgical purpose. The suction tube may also be rotatable relative to the handle. The suction tube electrode includes both a substantially blunt distal end for delivery coagulating energy to tissue and at least one aspiration port disposed along a side of the suction tube electrode. In yet another embodiment, the suction tube electrode is selectively extendible from the distal end of the handle. This embodiment of the coagulator may also include an elongated slot disposed in the suction tube electrode for slideably housing a needle electrode. Preferably, the needle electrode is selectively extendible from the blunt distal end of the suction electrode and selectively activateable to coagulate tissue as needed for precise dissection.

In still yet another embodiment of the present disclosure, the coagulator includes a selectively activateable valve for regulating the flow of surgical fluids and debris through the aspiration port. Preferably, the valve includes a generally arcuate sleeve which is rotated within the suction tube electrode to regulate the flow through the aspiration port.

These and other objects will be more clearly illustrated below by the description of the drawings and the detailed description of the various embodiments.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure.

FIG. 4 is a perspective view of an alternate embodiment of a surgical coagulator in accordance with the present disclosure having a selectively extendible needle electrode and a selectively rotatable aspiration port disposed at a distal end thereof; and FIG. 5 is a perspective view of an alternate embodiment of a surgical coagulator in accordance with the present disclosure having a side aspiration port located at a distal end thereof and a selectively adjustable control valve for regulating the amount of suction through the aspiration port.

DETAILED DESCRIPTION

Figure 1A:
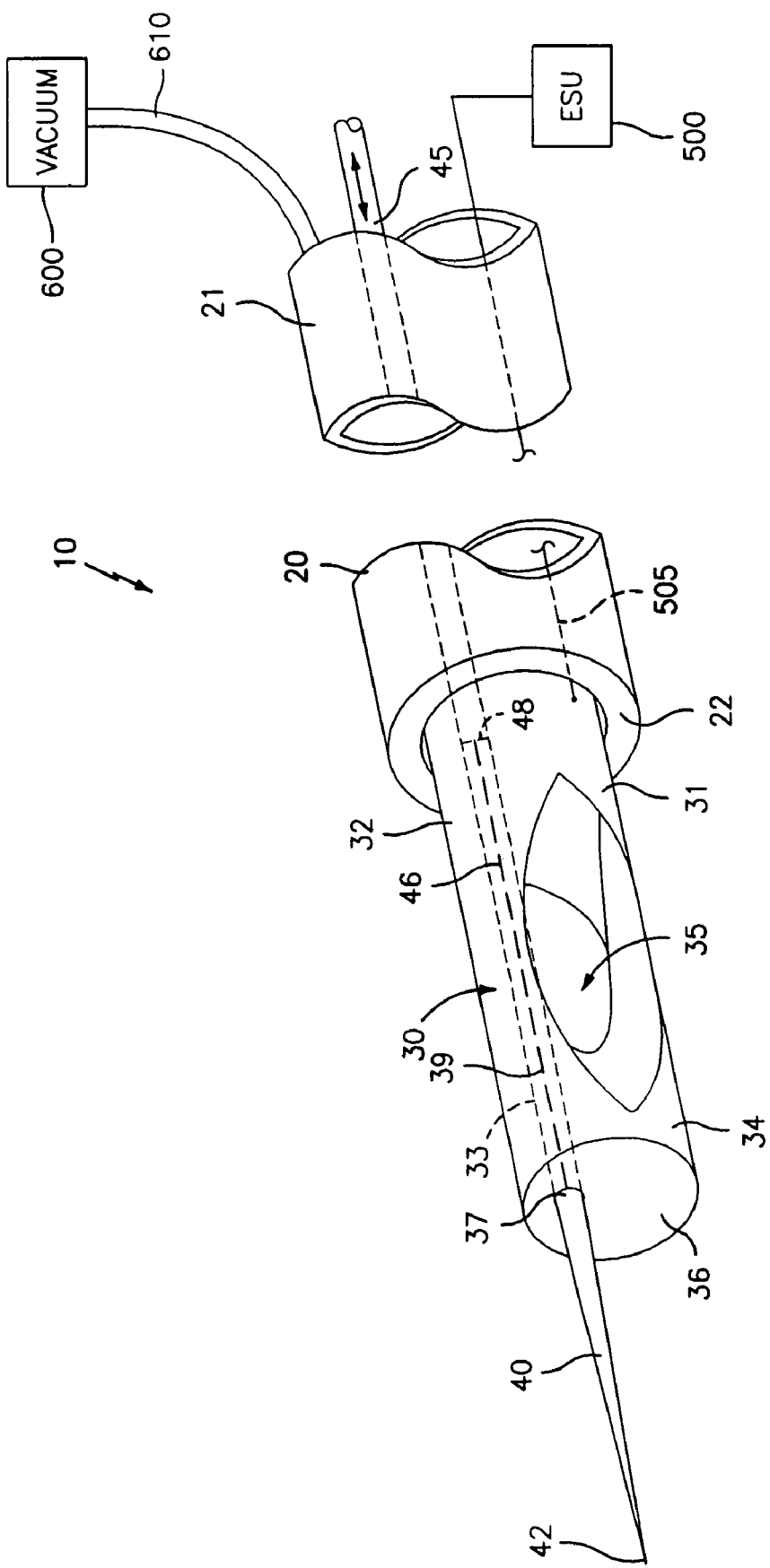
FIG. 1A is a perspective view of one embodiment of a surgical coagulator in accordance with the present disclosure showing a dissecting needle electrode in an extended position.

Preferred embodiments of the presently disclosed electrosurgical instrument will now be described in detail with reference to the drawing figures wherein like reference numerals identify similar or identical elements. As used herein, the term "distal" refers to that portion of the instrument which is further from the user while the term "proximal" refers to that portion of the instrument which is closer to the user.

FIG. 1A sets forth a perspective view of an electrosurgical coagulator constructed in accordance with the present disclosure and generally referenced by numeral 10. Coagulator 10 includes a handle 20 having proximal and distal ends 21 and 22, respectively, and an elongated tube-like electrode or suction tube electrode 30 which extends from the distal end 22. Suction tube electrode 30 includes a closed and substantially blunt distal end 36 which is dimensioned for use during gross dissection or blunt dissection. It is envisioned that the distal end 36 may be rounded or include a pattern of protuberances to facilitate coagulation of tissue at or adjacent the distal end 36 when activated. Suction tube electrode 30 is electrically interfaced to a source of electrosurgical energy such as an electrosurgical generator (ESU) 500 via cable 505. As schematically shown in FIG. 1A, the ESU 500 may include one or more electrical connections 505 to supply electrosurgical energy to the suction tube 30. As explained in more detail below, the ESU 500 may include one or more switches to control the amount of electrosurgical energy delivered through the suction tube electrode 30 and to the tissue. A return pad (not shown) may be utilized to complete the electrical circuit through the patient.

Suction tube electrode 30 also includes an elongated slot 33 disposed therethrough which extends generally from the distal end 36 the tube electrode 30 to a proximal end 32 of the tube electrode 30. Slot 33 is dimensioned to house a needle or wire electrode 40 which is selectively extendible from an aperture 37 disposed in the distal end 36 of the suction tube electrode 30. Needle electrode 40 is preferably tapered to form a point 42 at the end thereof to facilitate delicate and precise dissection of tissue. One or more wires or electrical interfaces 39 are connected to the needle electrode 40 to communicate electrosurgical energy from the ESU 500. It is envisioned that the needle electrode 40 may be independently energizable from to the suction tube electrode 30 or energized concurrently through the same electrical interface. Alternatively, the needle electrode 40 could be isolated from the suction tube electrode 30 depending upon a particular purpose, e.g., to create a different surgical effect on tissue when activated or to create a bipolar electrical arrangement. Several envisioned embodiments are explained in more detail below.

As mentioned above, the needle electrode 40 is selectively extendible from the distal end 36 of the suction tube electrode 30. More particularly, the coagulator 10 may include one or more control rods 45 which allow a user to selectively advance the needle electrode 40 from the distal end 36 to facilitate delicate dissection and coagulation of tissue and selectively retract the needle electrode 40 to grossly dissect and coagulate tissue using the blunt distal end 36 of the suction tube electrode 30. In one embodiment, the needle electrode 40 is attached to a distal end 48 of the control rod 45 by a control wire 46 which operates to extend and retract the needle electrode 40 within elongated slot 33. It is envisioned that the control rod 45 may be dimensioned to both mechanically advance and retract the needle electrode 40 and also electrically connect the needle electrode 40 (and the suction tube 30) to the ESU 500. The needle electrode may be manufactured by plant cutting a small gauge wire which may be made from a refractory alloy or the like.

Preferably, the needle electrode 40 and the suction tube electrode 30 are made from flexible and/or malleable materials to give the user additional control of the coagulator 10 during use. It is contemplated that the needle electrode 40 and the suction tube electrode 30 may be made from the same material or different materials depending upon a particular purpose. For example, the needle electrode 40 could be made from a more resilient material to facilitate delicate dissection or a refractory material to prevent melting of the electrode during use.

The suction tube electrode 30 also includes at least one aspiration port 35 disposed through a side 31 thereof. More particularly and as best shown in FIG. 1A, the suction tube electrode 30 is preferably connected to a source of negative pressure, i.e., vacuum 600, which draws air and fluid into the aspiration port 35 and into the vacuum via hose 610 upon activation. Preferably, the aspiration port 35 is dimensioned to facilitate removal of surgical fluids and debris from the surgical site. More particularly, the aspiration port 35 may be chamfered, beveled or some other advantageous shape to create a smooth fluid stream therethrough and into the suction tube electrode 30 when activated enabling the coagulator 10 to operate in a similar fashion to a suction wand.

It is envisioned that providing the aspiration port(s) 35 on the side of the suction tube electrode 30 will significantly reduce the chances of the coagulator 10 clogging during use. More particularly, the closed distal end 36 of the suction tube electrode 30 and the needle electrode 40 both remain free of debris buildup and clogging due to the negative pressure or suction redirecting fluid and debris away from the needle electrode 40 and the distal end 36 of the suction tube electrode 30 and into the side aspiration port(s) 35. As can be appreciated, a series of aspiration ports 35 may be disposed along the length of the suction tube electrode 30 depending upon a particular purpose.

Figure 1B:
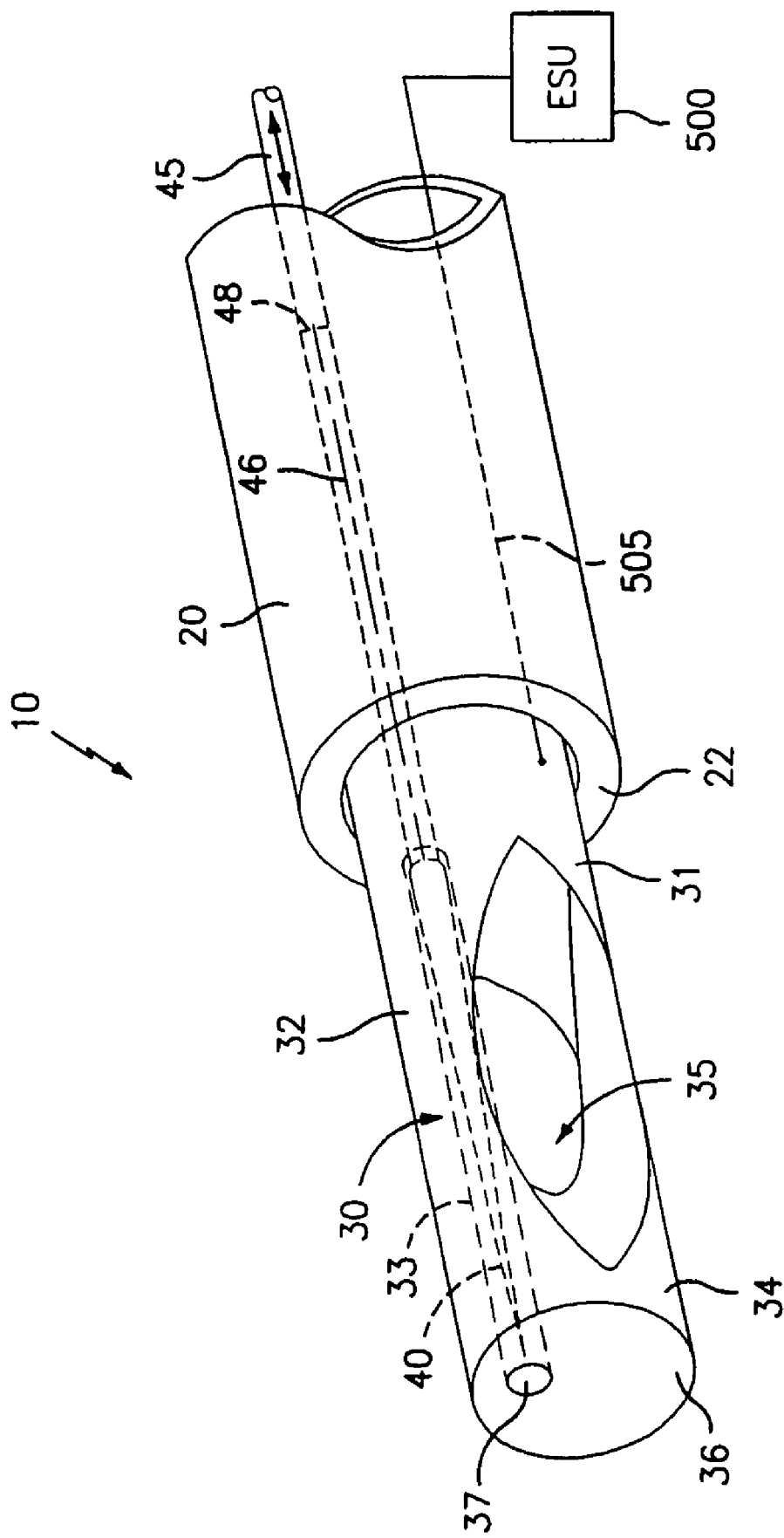
FIG. 1B is a perspective view of the embodiment of FIG. 1 showing the dissecting needle electrode in a retracted position.

As mentioned above and as best shown in FIG. 1B, the needle electrode 40 is selectively extendible and retractable within elongated slot 33 and relative to the distal end 36 of the suction tube electrode 30 via control rod 45. It is envisioned that the coagulator 10 may be configured such that upon extension of the needle electrode 40 energy is automatically switched from the suction tube electrode 30 to the needle electrode 40. Upon retraction, the energy switches back to the suction tube electrode 30 for blunt dissection. It is envisioned that a mechanical, electromechanical or simply electrical switch may be employed to accomplish this purpose. A seal or the like (not shown) may be employed to prevent surgical fluid and/or debris from entering slot 33.

Figure 2:
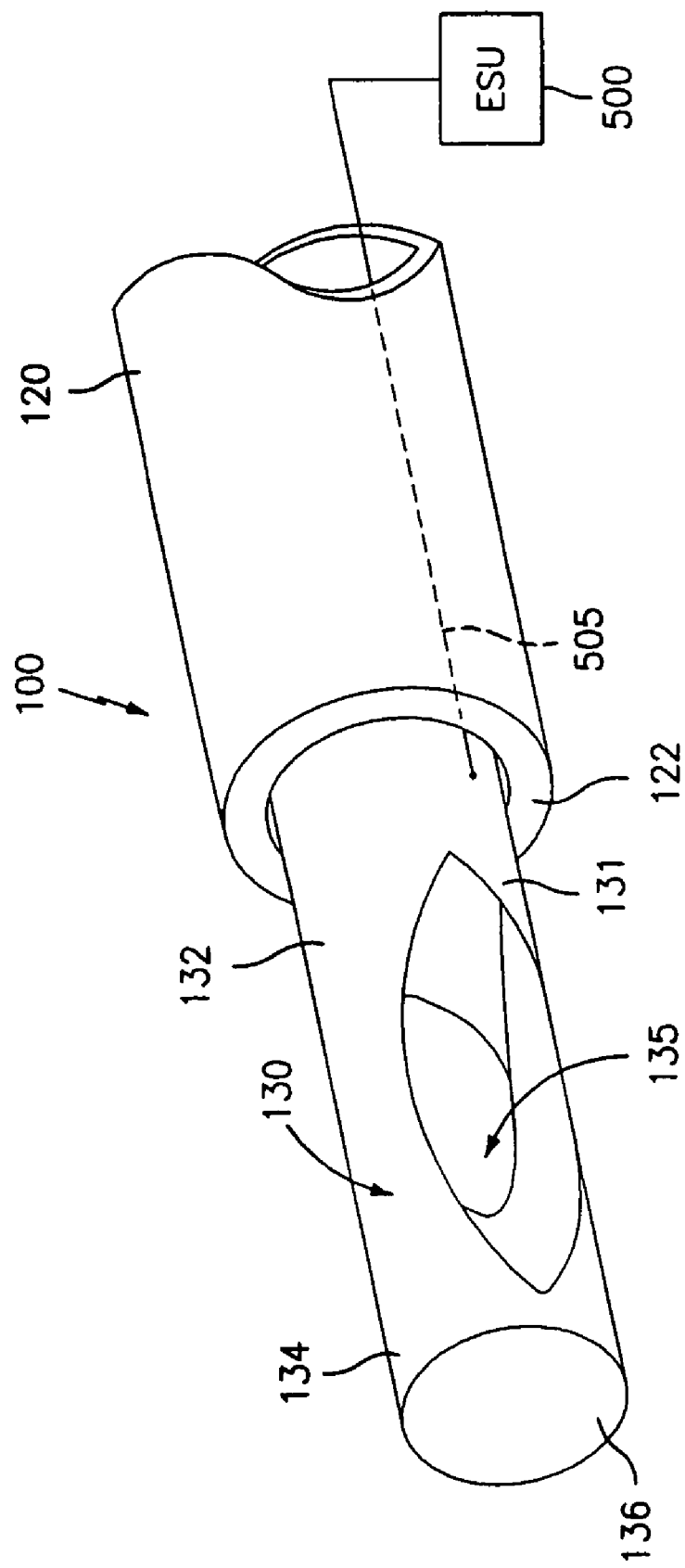
FIG. 2 is a perspective view of an alternate embodiment of a surgical coagulator in accordance with the present disclosure having a blunt dissector at a distal end thereof and a side aspiration port.

FIG. 2 shows an alternate embodiment of a coagulator 100 according to the present disclosure which includes a handle 120 having an elongated suction tube electrode 130 extending therefrom. Suction tube electrode 130 includes a substantially blunt distal end 136 and an aspiration port 135 disposed through a side 131 thereof. The suction tube electrode 130 is connected to ESU 500 via electrical connection 505 to allow selective activation of the suction tube electrode 130 to coagulate tissue. Preferably, the distal end 136 of the suction tube electrode 130 is dimensioned to facilitate gross coagulation and dissection of tissue. As mentioned above, locating the aspiration port(s) 135 along the side 131 of the suction tube electrode 130 reduces the likelihood of coagulum building up at the distal end 136 due to the aspiration port 135 clogging during use.

Figure 3:
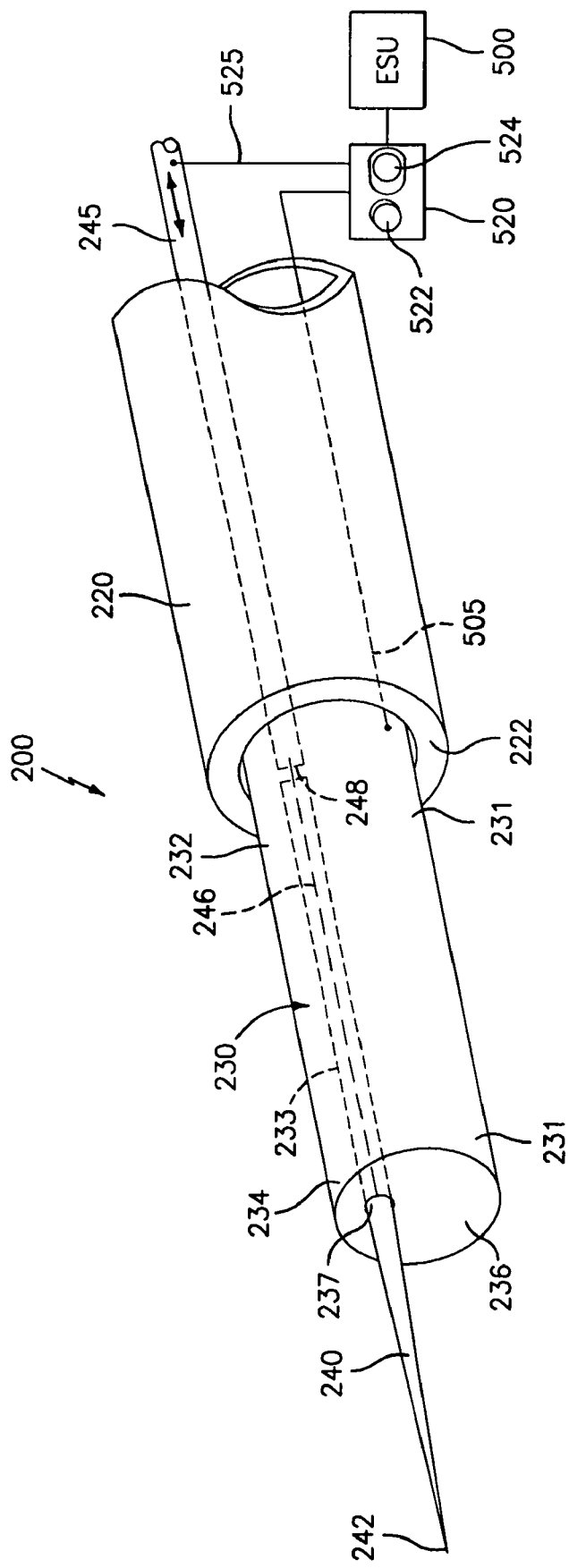
FIG. 3 is a perspective view of an alternate embodiment of a surgical coagulator in accordance with the present disclosure having a closed-end dissector at a distal end of the handle and a selectively extendible needle electrode extending from the distal end of the closed-end dissector.

FIG. 3 shows yet another embodiment of a coagulator 200 according to the present disclosure which includes a control switch 520 which regulates the electrosurgical energy to the needle electrode 240 and the suction tube electrode 230. More particularly, the control switch 520 includes a plurality of switches 522 and 524 which regulate, measure, monitor and/or control one or more of the following electrical or electromechanical parameters: electrical intensity, voltage, current, pulse rate, waveform, temperature and impedance. It is envisioned that the control switch 520 may cooperate with one or more sensors (not shown) to regulate certain parameters. A rotating or sliding type switch may be employed to accomplish this purpose. A series of computer algorithms may also be utilized to regulate, control and/or monitor the sensors or the switches to optimize or control various surgical effects. As mentioned above, the same control switch 520 may regulate both electrodes 230 and 240 or a second control switch may control either electrode 230 or 240 independently. Each electrode 230 and 240 is connected to the control switch 520 by a lead or electrical connection 505 and 525, respectively.

It is envisioned that the needle electrode 240 may be automatically energized upon extension and deactivated upon retraction. Similarly, the control switch 520 may deactivate the suction tube electrode 230 when the needle electrode 240 is extended and activated and automatically reactivate the suction tube electrode 230 when the needle electrode 240 is deactivated. It is contemplated that the user may selectively interchange between electrodes 230 and 240 simply by extending and retracting the needle electrode 240 while continually actuating an activation switch, e.g., footswitch or hand switch (not shown). It is also contemplated that the needle electrode 240 and the suction tube electrode 230 can be pre-set or pre-programmed to deliver different surgical effects or different energy intensities depending upon a particular purpose or to facilitate dissection.

FIG. 4 shows yet another coagulator 300 according to the present disclosure wherein the suction tube 330 is slidingly and rotatably received within a channel 325 disposed in the distal end 322 of the handle 320. More particularly, the suction tube 330 is positioned within the channel 325 to permit a user to slidingly extend and rotate the suction tube electrode 330 as needed during surgery. A control rod 347 is mechanically coupled to the proximal end 332 of the suction tube 330 and is manipulatable by the user to extend, retract and/or rotate the suction tube 330 to facilitate dissection and aspiration of the operating area. More particularly, the user can manipulate the needle electrode 340 via the control rod 345 (which operates in a similar manner as described above) and/or via the control rod 347 which would allow the user to rotate the needle electrode 340 within the operating area. In addition, the aspiration port(s) 335 can be rotated, extended and retracted into position to aspirate and clean the operating area during use. Moreover, the suction tube electrode 330 can be manipulated into position to facilitate gross dissection of tissue.

FIG. 5 shows yet another embodiment of a coagulator 400 according to the present disclosure which includes a control valve disposed over the aspiration port 435. More particularly, the coagulator 400 includes an elongated sleeve 450 which is interleaved within the inner periphery of the suction tube 430. The sleeve 450 is selectively rotatable from a first, open position which does not impede the influx of surgical fluids and debris through the aspiration port 435 to a series of subsequent positions in which the sleeve 450 incrementally impedes the flow of fluids through the aspiration port 435 and regulates the overall suction energy of the aspiration port 435. It is envisioned that the sleeve 450 may be configured in a different manner to accomplish the same purpose, i.e., the sleeve 450 may be selectively extendible over the aspiration port 435 to regulate suction.

From the foregoing and with reference to the various figure drawings, those skilled in the art will appreciate that certain modifications can also be made to the present disclosure without departing from the scope of the present disclosure. For example, it is contemplated that the presently disclosed coagulator may be manufactured such that the coagulator is disposable, reusable or reposable. It is envisioned that a variety of different or interchangeable needle electrodes could be selectively attached to the distal end of the control rod depending upon a particular purpose or to meet a particular surgical need. It is also envisioned that the coagulator may be designed such that the tip of the needle electrode is removably engageable thus allowing a surgeon to selectively engage variously-sized and variously-shaped tips for dissection purposes.

It is contemplated that positioning the aspiration/ventilation ports 35 on the side of the suction tube electrode 30 is effective at eliminating debris from the surgical field and limits eschar buildup. As can be appreciated, positioning multiple ports 35 around the circumference of the suction tube electrode 30 further reduces the chances of obstructing the suction tube. It is also envisioned that by allowing free flow of fluid through the tube will essentially cool the suction electrode and dissipate heat thus further reducing overall eschar buildup around the suction ports 35.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

The invention claimed is:

1. An electrosurgical suction coagulator, comprising:
    a handle having an elongated tube electrode extending from a distal end thereof, said elongated tube electrode including:
        a substantially blunt and closed distal end;
        an elongated slot disposed therethrough that slidingly receives a needle electrode, said needle electrode being selectively extendible relative to said closed distal end;
            at least one aspiration port disposed along a side of the elongated tube electrode, wherein the at least one aspiration port is chamfered; and
        a selectively activateable valve operable to regulate the flow through said aspiration port, said valve including a generally arcuate sleeve that is rotated within the elongated tube electrode to regulate the flow through said aspiration port.

2. An electrosurgical suction coagulator according to claim 1, wherein the needle electrode is substantially flexible.

3. An electrosurgical coagulator according to claim 1, wherein the elongated tube electrode is substantially malleable.

4. An electro surgical suction coagulator according to claim 1, wherein the elongated tube electrode includes one aspiration port that extends generally from a proximal end of the elongated tube electrode to the distal end of the elongated tube electrode.

5. An electrosurgical suction coagulator according to claim 1, wherein the elongated tube electrode includes one aspiration port that extends transversally through said elongated tube electrode.

6. An electrosurgical suction coagulator according to claim 1, further comprising a control switch operable to activate at least one of said elongated tube electrode and said needle electrode.

7. An electrosurgical suction coagulator according to claim 6, wherein said control switch includes first and second switches, said first switch operable to control the electrosurgical energy delivered to the elongated tube electrode and said second switch operable to control the electrosurgical energy delivered to the needle electrode.

8. An electrosurgical suction coagulator according to claim 7, wherein said elongated tube electrode and said needle electrode are energized by the same said first switch and controlled by said second switch which sets the energy delivered to the needle electrode based upon the position of the extendable needle electrode.

9. An electrosurgical suction coagulator according to claim 6, wherein said control switch activates said elongated tube electrode when said needle electrode is in a retracted position and said switch activates said needle electrode when said needle electrode is in an extended position.

10. An electrosurgical suction coagulator according to claim 6, wherein a sliding or rotating control sets the intensity of the electrosurgical effect.

11. An electrosurgical suction coagulator according to claim 1, wherein the needle electrode is formed by plant cutting a small gauge wire.

12. An electrosurgical suction coagulator according to claim 11, wherein said small gauge wire is made at least partially from a refractory alloy.

13. An electrosurgical suction coagulator, comprising:
    a handle having an elongated tube electrode extending from a distal end thereof, said elongated tube electrode including:
        a substantially blunt and closed distal end;
        an elongated slot disposed therethrough for slideably receiving a needle electrode, said needle electrode being selectively extendible relative to said closed distal end;
    at least one aspiration port disposed along a side of the elongated tube electrode; and
    a selectively activateable valve for regulating the flow through said aspiration port, wherein said valve includes a generally arcuate sleeve which is rotated within the elongated tube electrode to regulate the flow through said aspiration port.

* * * * *